US012805713B2

(12) United States Patent
Rayman et al.

(10) Patent No.: US 12,805,713 B2
(45) Date of Patent: Nov. 24, 2026

(54) PHARYNGEAL AND AURAL EXAMINATION APPARATUS AND SYSTEM

(71) Applicant: Alai Medicine Inc., London (CA)

(72) Inventors: Reiza Rayman, London (CA); Michael Konstantine Lavdas, London (CA); Meghan Leigh Thorne, Burlington (CA)

(73) Assignee: Alai Medicine Inc., London (CA)

( * ) Notice: Subject to any disclaimer, the term of this patent is extended or adjusted under 35 U.S.C. 154(b) by 796 days.

(21) Appl. No.: 18/187,347

(22) Filed: Mar. 21, 2023

(65) Prior Publication Data

US 2023/0301502 A1 Sep. 28, 2023

Related U.S. Application Data

(60) Provisional application No. 63/322,515, filed on Mar. 22, 2022.

(51) Int. Cl.
*A61B 5/00* (2006.01)
*A61B 1/00* (2006.01)
(Continued)

(52) U.S. Cl.
CPC ............ *A61B 1/24* (2013.01); *A61B 1/00124* (2013.01); *A61B 1/07* (2013.01); *A61B 1/227* (2013.01);
(Continued)

(58) Field of Classification Search
CPC ......... A61B 1/24; A61B 1/00124; A61B 1/07; A61B 1/227; A61B 5/0008; A61B 5/01;
(Continued)

(56) References Cited

U.S. PATENT DOCUMENTS 3,349,764 A * 10/1967 Edinger .................. A61B 1/24 600/212
3,638,644 A * 2/1972 Reick ..................... A61B 1/267 600/199

(Continued)

FOREIGN PATENT DOCUMENTS

CN 111759263 A * 10/2020 .............. A61B 5/01
KR 101848159 B1 * 4/2018 ............ A61B 13/00

(Continued)

*Primary Examiner* — May A Abouelela

(57) ABSTRACT

An apparatus for performing a medical examination is disclosed. The apparatus includes a mounting interface configured to couple to a smartphone including a camera and illuminator. A depressor blade has a proximal end demountably attachable to the mounting interface and configured to displace a patient's tongue to provide access for illumination of a patient's pharynx by the illuminator, thus facilitating capture of an image of the pharynx by the camera. An otoscope attachment has a proximal end demountably attachable to the mounting interface, the ostocope attachment terminating in a speculum shaped for insertion into a patient's ear. One or more optical elements are disposed on the ostocope attachment and are configured to direct illumination provided by the illuminator into the patient's ear, thus facilitating capture of an image of the patient's ear by the camera.

36 Claims, 6 Drawing Sheets

(51) Int. Cl.
*A61B 1/07* (2006.01)
*A61B 1/227* (2006.01)
*A61B 1/24* (2006.01)
*A61B 5/01* (2006.01)
*A61B 13/00* (2006.01)

(52) U.S. Cl.
CPC .............. *A61B 5/0008* (2013.01); *A61B 5/01* (2013.01); *A61B 13/00* (2013.01)

(58) Field of Classification Search
CPC ..... A61B 13/00; A61B 5/0013; A61B 5/0077; A61B 5/7475; A61B 5/6898
See application file for complete search history.

(56) References Cited

U.S. PATENT DOCUMENTS 3,826,248 A * 7/1974 Gobels ................... A61B 1/267 600/199
3,848,587 A * 11/1974 McDonald ............... A61B 1/07 600/187
3,916,881 A * 11/1975 Heine .................. A61B 1/0669 600/212
4,643,172 A * 2/1987 Taff ......................... A61B 1/24 600/203
4,807,599 A * 2/1989 Robinson ................. A61B 1/07 433/29
4,996,976 A * 3/1991 Nakagawa ............... A61B 1/24 362/572
5,060,633 A * 10/1991 Gibson .................. A61B 1/267 600/199
5,318,009 A * 6/1994 Robinson ........... A61B 1/00032 362/120
5,656,014 A * 8/1997 Rooney .................. A61B 13/00 600/240
5,897,492 A * 4/1999 Feller ..................... A61B 13/00 206/363
D422,081 S * 3/2000 Wolff ............................. D26/37
6,059,723 A * 5/2000 Davis ....................... A61B 1/24 600/245
6,257,238 B1 * 7/2001 Meah ....................... A61B 1/24 128/200.26
6,520,909 B1 * 2/2003 Rankins ............. A61B 1/00105 600/196
8,684,577 B2 * 4/2014 Vayser ................... A61B 17/02 362/333
9,386,913 B2 7/2016 Holland
9,504,417 B2 * 11/2016 Shimoyama ........... A61C 19/04
10,231,667 B2 * 3/2019 Mathew ............... A61B 5/7278
10,603,540 B2 * 3/2020 Ikeda .................... A61B 5/4552
11,696,680 B2 * 7/2023 Elson .................... A61B 5/6898 600/200
12,070,194 B2 * 8/2024 Mock ...................... H04N 7/183
2002/0183596 A1 * 12/2002 Bruno .................... A61B 13/00 600/240
2003/0019769 A1 * 1/2003 Babakitis ............... A61B 13/00 206/484
2003/0100819 A1 * 5/2003 Newman .............. A61B 5/0088 600/300
2004/0019293 A1 * 1/2004 Schweitzer, Jr. .. A61B 5/14552 600/549
2007/0055112 A1 * 3/2007 Lesko .................. A61B 1/0669 600/241
2007/0129607 A1 * 6/2007 Ashfaque ............... A61B 1/267 600/190
2009/0171155 A1 * 7/2009 Tsunoda ................... A61B 1/24 600/114
2009/0209849 A1 * 8/2009 Rowe ................. A61B 5/14539 340/8.1
2010/0305409 A1 * 12/2010 Chang ...................... A61B 1/05 600/240
2011/0190666 A1 * 8/2011 Friedland ............... A61B 13/00 600/590
2011/0209715 A1 * 9/2011 Burdumy ................. A61C 5/90 128/861
2011/0240036 A1 * 10/2011 Westbrook ............. A61B 13/00 128/845
2011/0240040 A1 * 10/2011 Westbrook ............. A61B 90/14 128/860
2012/0041268 A1 * 2/2012 Grey ...................... A61B 1/267 600/199
2013/0096457 A1 * 4/2013 Qiu ........................ A61B 1/267 600/549
2014/0180006 A1 * 6/2014 Gov-Ari ................ A61B 13/00 600/120
2015/0087926 A1 * 3/2015 Raz .......................... A61B 5/01 600/301
2015/0185086 A1 * 7/2015 Al-Faifi ................... G01K 7/22 374/10
2016/0338590 A1 * 11/2016 Sagalovich ........ A61B 1/00066
2017/0027432 A1 * 2/2017 Wachs ..................... A61B 1/06
2017/0071463 A1 * 3/2017 Xiao ...................... A61B 13/00
2017/0112671 A1 * 4/2017 Goldstein ............ H04R 25/554
2017/0150878 A1 * 6/2017 Swift ................. A61B 1/00032
2017/0280987 A1 * 10/2017 Weiandt ................. A61B 1/247
2017/0312117 A1 * 11/2017 Shah ........................ A61B 5/01
2018/0160887 A1 * 6/2018 Hefez .............. A61B 1/000094
2018/0353073 A1 * 12/2018 Boucher .................. A61B 5/05
2019/0046168 A1 * 2/2019 Harris .................. A61B 5/0077
2019/0200850 A1 * 7/2019 Holland ................... A61B 1/07
2019/0216402 A1 * 7/2019 Sayani ................... A61B 1/233
2020/0168329 A1 * 5/2020 Solie ...................... G16H 40/67
2021/0059512 A1 * 3/2021 Vargo ................. A61B 1/00066
2022/0000342 A1 * 1/2022 Knecht ................ A61B 1/0014
2022/0133141 A1 * 5/2022 Mock ...................... A61B 1/227 348/77
2022/0361741 A1 * 11/2022 Okiyama ............. A61B 5/0077
2023/0172486 A1 * 6/2023 Shouldice ............ A61B 5/1076 600/301
2023/0248239 A1 * 8/2023 Mersinger .............. A61B 5/022 600/301
2024/0293019 A1 * 9/2024 Harris ..................... A61B 1/042
2024/0315545 A1 * 9/2024 Un ........................... A61B 1/24

FOREIGN PATENT DOCUMENTS

KR 102237060 B1 * 4/2021 ............. A61B 13/00
WO WO-2012021937 A1 * 2/2012 ............... A61B 1/32
WO WO-2013156999 A1 * 10/2013 ........... A61B 5/0013
WO WO-2018049479 A1 * 3/2018 ......... A61B 1/00103
WO WO-2021085443 A1 * 5/2021 ............... A61B 1/05
WO WO-2022005043 A1 * 1/2022 ............... A61B 1/06

* cited by examiner

PHARYNGEAL AND AURAL EXAMINATION APPARATUS AND SYSTEM

BACKGROUND

1. Field

This disclosure relates generally to medical devices and more specifically to an apparatus for performing a medical examination of a patient's pharynx or a patient's ear.

2. Description of Related Art

The administering of medical services may involve a physician using one or more common physician tools such as an otoscope for ear examination or an ophthalmoscope for examining a patient's eyes. A physician may also make use of a light and a tongue depressor to examine a patient's throat or a thermometer to take the patient's temperature. Alternatively a physician may use an otoscope to examine a patient's ear, ear canal, or eardrum. Such tools are generally available to a physician and can be employed when meeting with a patient for an in-person consultation. For remote patient consultation, the physician may be hampered by being unable to visually examine the affected area using one or more of the above-mentioned common physician tools. Even for in-person consultation, a physician my prefer not to perform examinations that require close contact with a patient for fear of contracting a virus or other illness from the patient.

SUMMARY

In accordance with one disclosed aspect there is provided an apparatus for performing a medical examination of a patient's pharynx. The apparatus includes a mounting interface configured to mechanically couple to a smartphone, the smartphone including a camera and an illuminator. The apparatus also includes a depressor blade including a proximal end configured to demountably attach to the mounting interface, the depressor blade being configured to displace the patient's tongue to provide access for illumination of the pharynx by the illuminator. The illumination facilitates capture of an image of the pharynx by the camera. The apparatus also includes a temperature sensor disposed on the depressor blade for generating a temperature signal representing a temperature in the pharynx. The apparatus further includes a signal interface disposed within the mounting interface, the signal interface being configured to receive and transmit the temperature signal to the smartphone.

The depressor blade may include a signal connector located at the proximal end of the depressor blade, the signal connector being connected via a signal line to the temperature sensor, the signal connector being configured to connect to a corresponding interface connector on the mounting interface.

The signal connector and the interface connector may include one of corresponding Universal Serial Bus (USB) connector types, or a printed circuit board edge connector and corresponding socket connector.

The mounting interface may include a socket configured to receive and guide the proximal end of the depressor blade to cause the signal connector to connect to the interface connector.

The temperature sensor may be distally disposed proximate an underside of the depressor blade to facilitate thermal contact with the patient's tongue while the depressor blade displaces the patient's tongue.

The signal interface may include an electrical circuit for receiving the temperature signal and generating data representing the temperature signal, and a wireless transmitter for transmitting the data representing the temperature signal to the smartphone.

The signal interface may further include a power source operable to supply operating current to the electrical circuit and the wireless transmitter.

The mounting interface may be configured to mechanically couple to the smartphone such as to provide an unobstructed field of view for the illuminator and the camera.

The mounting interface may be configured to mechanically couple to the smartphone by one of magnetically coupling to the smartphone, one or more attachment features configured to clip the mounting interface to the smartphone, or an integrated smartphone case configured to receive and retain a smartphone.

The depressor blade may include a single-use depressor blade that is discarded after use.

The temperature sensor may be sealingly embedded within the depressor blade to facilitate cleaning for reuse of the depressor blade after being used to depress a patient's tongue.

At least a portion of the depressor blade may include one of a light transmissive material for transmitting at least a portion of the illumination to the pharynx, or one or more optical fibers extending along the depressor blade for transmitting at least a portion of the illumination to the pharynx.

The depressor blade may further include an attachment area configured to hold a pharyngeal swab for taking a sample from the pharynx of the patient.

The swab may include one of a pH test strip for sensing a pH associated with the pharynx, or a swab for taking a sample for sensing a pathogen within the pharynx.

A pharyngeal examination system may include the apparatus above and may further include a smartphone apparatus, the smartphone apparatus including a computer readable memory for storing program codes for directing a processor of the smartphone to execute functions on the smartphone to receive and display a temperature associated with the temperature signal transmitted by the apparatus.

The program codes may further direct the processor to generate a record associating the temperature with image data representing a captured image of the pharynx.

The program codes may further direct the processor to store the record in a data storage location accessible by the smartphone.

The program codes may further direct the processor to retrieve a plurality of records including image data and associated temperatures captured over a period of time, and display a series of views of the pharynx over the period of time for documenting a progression of a condition associated with the patient's pharynx.

The data storage location memory may include a remote storage location accessible via a data network.

The program codes may further direct the processor to stream image data over a data network for viewing by a remotely located health care worker.

In accordance with one disclosed aspect there is provided an apparatus for use with a smartphone for performing a medical examination of a patient's ear, the smartphone including a camera and an illuminator. The apparatus includes a mounting interface configured to mechanically couple to the smartphone. The apparatus also includes an otoscope attachment including a proximal end configured to demountably attach to the mounting interface, the otoscope attachment terminating in a speculum shaped for insertion into the patient's ear and including one or more optical elements disposed and configured to direct illumination provided by the illuminator of the smartphone into the ear and to capture and direct light back to the camera of the smartphone for producing an image of the ear. The apparatus further includes a temperature sensor distally disposed on the speculum for generating a temperature signal representing a temperature in the ear and a signal interface disposed within the mounting interface, the signal interface being configured to receive and transmit the temperature signal to the smartphone.

The otoscope attachment may include a signal connector located at the proximal end, the signal connector being connected via a signal line to the temperature sensor, the signal connector being configured to connect to a corresponding interface connector on the mounting interface.

The signal connector and the interface connector may include one of corresponding Universal Serial Bus (USB) connector types, or a printed circuit board edge connector and corresponding socket connector.

The mounting interface may include a socket configured to receive and guide the proximal end of the otoscope attachment to cause the signal connector to connect to the interface connector.

The temperature sensor may be distally disposed proximate an underside of the speculum to facilitate thermal contact with the patient's ear.

The signal interface may include an electrical circuit for receiving the temperature signal and generating data representing the temperature signal, and a wireless transmitter for transmitting the data representing the temperature signal to the smartphone.

The signal interface may further include a power source operable to supply operating current to the electrical circuit and the wireless transmitter.

The mounting interface may be configured to mechanically couple to the smartphone such that illumination generated by the illuminator of the smartphone is directed into the ear via the one or more optical elements and light captured by the one or more optical elements is directed toward the camera of the smartphone.

The mounting interface may be configured to mechanically couple to the smartphone by one of magnetically coupling to the smartphone, one or more attachment features configured to clip the mounting interface to the smartphone, or an integrated smartphone case configured to receive and retain a smartphone.

The otoscope attachment may include a single-use speculum cover that may be discarded after use.

The temperature sensor may be sealingly embedded within a tip of the speculum.

In accordance with another disclosed aspect, an ear examination system includes the apparatus above and a smartphone apparatus, the smartphone apparatus including a computer readable memory for storing program codes for directing a processor of the smartphone to execute functions on the smartphone to receive and display a temperature associated with the temperature signal transmitted by the apparatus.

The program codes may further direct the processor to generate a record associating the temperature with image data representing a captured image of the ear.

The program codes may further direct the processor to store the record in a data storage location accessible by the smartphone.

The program codes may further direct the processor to retrieve a plurality of records including image data and associated temperatures captured over a period of time, and display a series of views of the ear over the period of time for documenting a progression of a condition associated with the patient's ear.

The data storage location memory may include a remote storage location accessible via a data network.

The program codes may further direct the processor to stream image data over a data network for viewing by a remotely located health care worker.

Other aspects and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments.

DETAILED DESCRIPTION

Figure 1A:
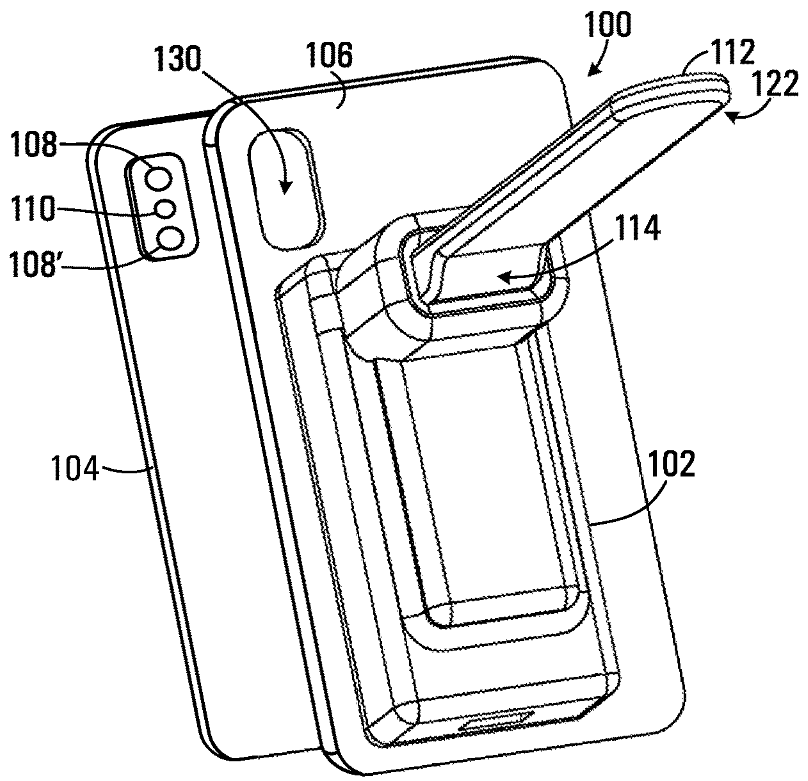
FIG. 1A is a perspective view of an apparatus for performing a medical examination of a patient's pharynx in accordance with one disclosed embodiment.

Referring to FIG. 1A, an apparatus for performing a medical examination of a patient's pharynx is shown generally at 100. The apparatus 100 includes a mounting interface 102, which is configured to mechanically couple to a smartphone 104. The smartphone 104 includes a camera 108 and an illuminator 110 and the mounting interface 102 is configured to mechanically couple to the smartphone 104 to provide an unobstructed field of view for the camera 108 and the illuminator 110. In the embodiment shown the camera 108 includes a wide angle imaging lens and the smartphone 104 also includes a second camera 108', which is configured with a telephone imaging lens. The smartphone 104 may process images from both cameras 108 and 108' to improve imaging and zoom capabilities of the smartphone. In other embodiments the smartphone 104 may have a single camera.

In the embodiment shown in FIG. 1A the mounting interface 102 includes a case 106 disposed to receive and retain the smartphone 104. The case 106 may be provided as an integral portion of the mounting interface 102 and a cutout 130 is included to provide the unobstructed field of view for the camera 108 and the illuminator 110. In other embodiments the coupling between the mounting interface 102 and the case 106 or the smartphone 104 may be via other means, such as a magnetic attachment or via one or more attachment features that are configured to clip the mounting interface 102 to the smartphone 104.

Figure 1B:
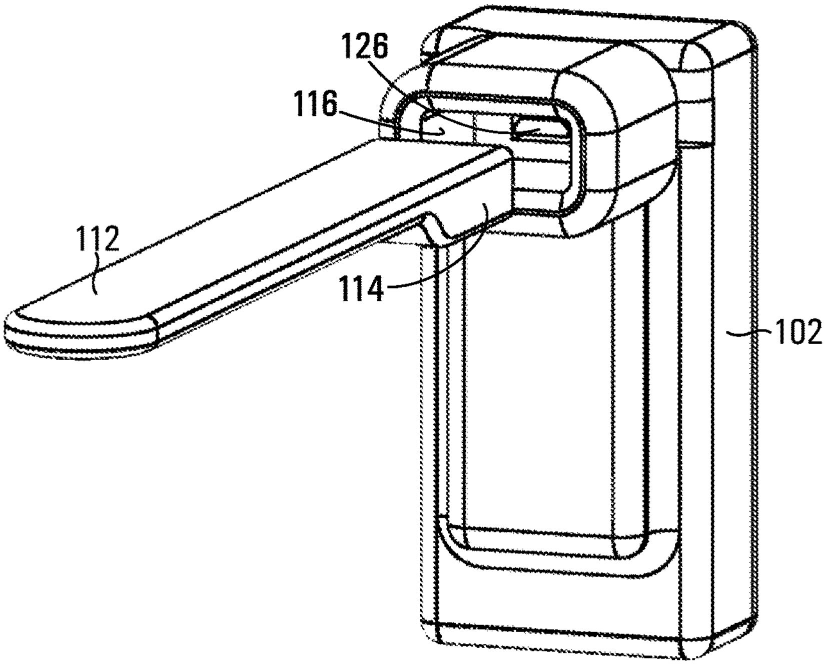
FIG. 1B is a perspective view of the apparatus of FIG. 1A showing a depressor blade detached from a mounting interface of the apparatus.

The apparatus 100 also includes a depressor blade 112, which has a proximal end 114 configured to demountably attach to the mounting interface 102. Referring to FIG. 1B, the mounting interface 102 includes a socket 116 configured to receive the proximal end 114 of the depressor blade 112 for demountably attaching the depressor blade to the mounting interface 102. In some embodiments the depressor blade 112 may be intended for a limited number or single use and may be discarded after use. In other embodiments the depressor blade 112 may be constructed to permit washing of at least a distal portion 122 of the depressor blade. In some embodiments at least a portion of the depressor blade 112 may be fabricated from a material that is light transmissive to aid in transmitting light generated by the illuminator 110. In other embodiments the depressor blade 112 may include a plurality of optical fibers that extend along the depressor blade for transmitting illumination.

Figure 1C:
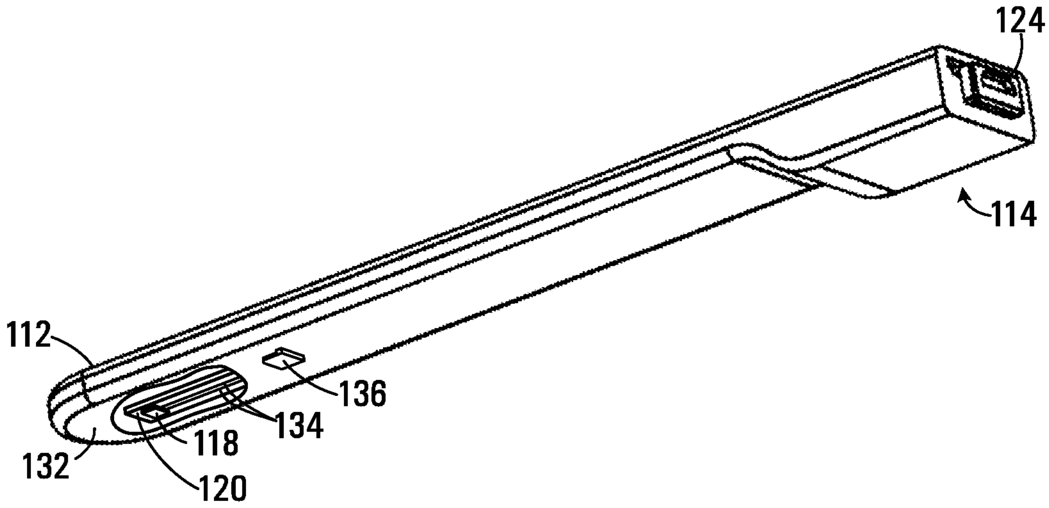
FIG. 1C is a further perspective view of the depressor blade shown in FIG. 1A and FIG. 1B.

Referring to FIG. 1C, the depressor blade 112 further includes a temperature sensor 118, which in this embodiment is embedded within the depressor blade proximate an underside surface 132 of the blade. The temperature sensor 118 is shown in partially cut-away detail in FIGS. 1C and 1*s* mounted on to a circuit substrate 120 that extends along between the temperature sensor and the proximal end 114 of the depressor blade 112. In this embodiment the temperature sensor 118 is disposed at the distal end 122 of the depressor blade 112 and is located close to the underside surface 132 to promote thermal conduction to the sensor. The temperature sensor 118 is thus sealingly embedded within the depressor blade, which facilitates cleaning for reuse of the depressor blade after being used to depress a patient's tongue. The temperature sensor 118 generates a temperature signal which is transmitted via a signal line including conductors 134 that extend along the circuit substrate 120 back to a signal interface described in more detail below. The signal interface is disposed within the mounting interface 102 and receives the temperature signal from the temperature sensor 118.

In the embodiment shown in FIG. 1C, the depressor blade 112 further comprises an attachment area 136 configured to hold a pharyngeal swab (not shown) for taking a sample from the pharynx of a patient. As an example, the swab may be a pH test strip for sensing a pH associated with the pharynx or a swab for taking a sample for sensing a pathogen within the pharynx.

Still referring to FIG. 1C, in this embodiment the circuit substrate 120 of the depressor blade 112 terminates in a connector 124 at the proximal end 114 of the depressor blade. The connector 124 is configured to connect to a corresponding interface connector 126 disposed within the socket 116 of the mounting interface 102. The connectors 124 and 126 connect the signal line conductors 134 from the temperature sensor 118 to signal interface circuitry that is disposed within the mounting interface 102. In this embodiment the connector 124 and corresponding interface connector 126 are implemented as Universal Serial Bus (USB) mini connectors. In other embodiments, connectors other than a USB connector may be used in other embodiments such as a printed circuit board edge connector and corresponding socket connector, for example.

Figure 1D:
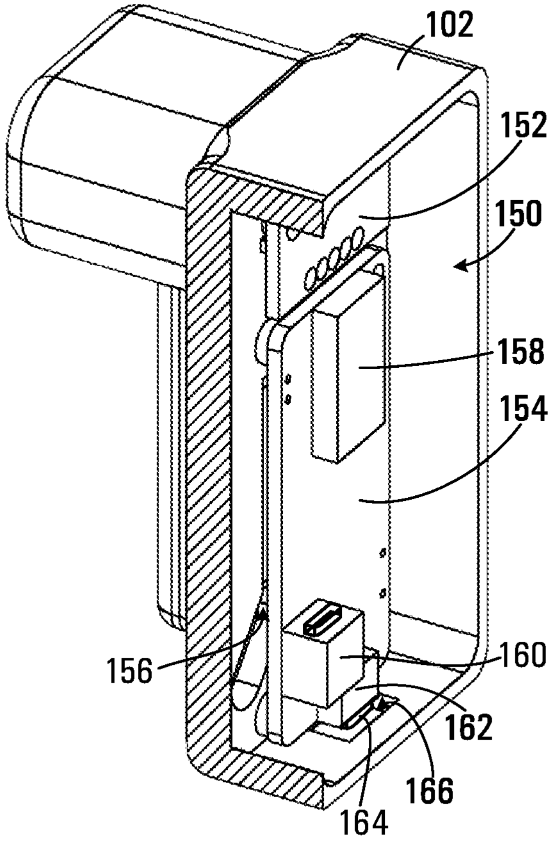
FIG. 1D is a partial sectional view of the apparatus of FIG. 1A with a rear cover of the apparatus removed.

Referring to FIG. 1D, the mounting interface 102 is shown in a partial sectional view with a rear cover removed to reveal signal interface circuitry 150 housed within the mounting interface. The signal interface circuitry 150 includes a distribution board 152 and a processor board 154. The distribution board 152 carries the interface connector 126 (shown in FIG. 1B) and connects the temperature signal produced by the temperature sensor 118 to the processor board 154. A power source in the form of a rechargeable battery 156 for supplying operating current to the processor board 154 is disposed in a recess behind the processor board 154. The processor board 154 includes a microcontroller 158, a wireless transmitter 160, and charger circuitry 162. The charger circuitry 162 includes a connector 164 that is accessible via an opening 166 in the mounting interface 102 for connecting to an external power source for charging the battery 156. The connector may be a USB mini connector that connects to a standard 5 Volt plug-in USB charger, for example. In the embodiment described herein the wireless transmitter 160 is implemented as a Bluetooth wireless transmitter, but may be implemented using other transmission protocols such as a near-field communication (NFC).

Figure 2:
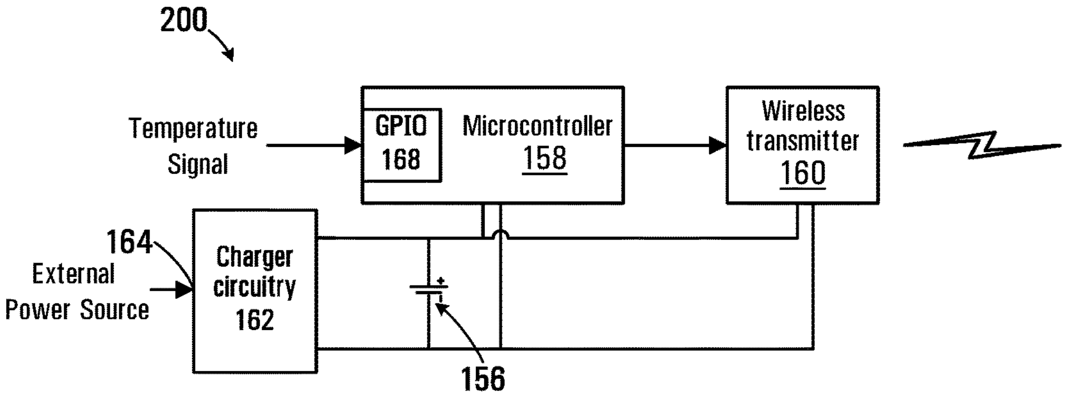
FIG. 2 is an electrical circuit schematic for a processor board shown in FIG. 1D.

Referring to FIG. 2, an electrical circuit of the processor board 154 is shown schematically at 200. The battery 156 provides operating power to both the microcontroller 158 and the wireless transmitter 160. In this embodiment the battery 156 is implemented as a rechargeable battery that may be periodically charged by an external power source connected to the charger circuitry 162 via the connector 164. The microcontroller 158 includes an on-chip general purpose input/output (GPIO) 168 for receiving the temperature signal from the temperature sensor 118. The microcontroller 158 is connected to the wireless transmitter 160 for transmitting Bluetooth signals.

Figure 3:
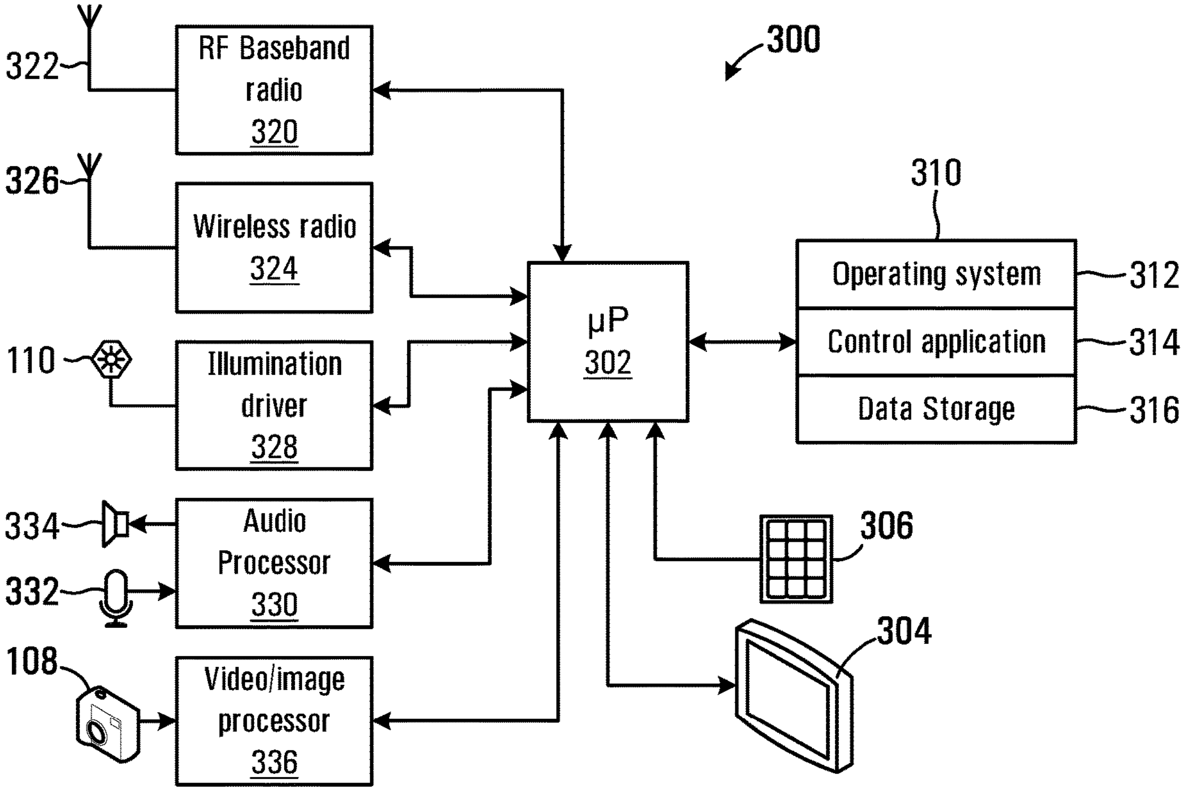
FIG. 3 is a block diagram of a typical smartphone processor circuit.

A block diagram of a typical smartphone processor circuit is shown generally at 300 in FIG. 3. Referring to FIG. 3, the processor circuit 300 includes a microprocessor 302, a display 304, and an input device 306 for receiving user input. In most embodiments the input device 306 is provided as touch screen display 304. The processor circuit 300 also includes a memory 310 for storing data associated with operating system functions and/or applications that are running on the device. The memory 310 may be implemented using non-volatile flash memory or other memory type. The memory 310 may be used for storing program codes and/or data and in the embodiment shown includes an operating system storage location 312, a storage location 314 for storing program codes for implementing a control application for interfacing with the apparatus 100, and a data storage location 316 for storing data generated during operation of the apparatus. The operating system storage location 312 stores codes for directing the microprocessor 302 to implement an operating system, which may be an Android™ based operating system, an iOS based operating system, or any other operating system.

The processor circuit 300 further includes a RF baseband radio 320 and antenna 322 for connecting to a mobile telecommunications network. The RF baseband radio 320 may be configured to provide data communications using any of a variety of communications standards including 2G, 3G, 4G, and/or 5G or any other communications standards. The processor circuit 300 also includes a wireless radio 324 and antenna 326 for connecting to local networks such as an IEEE 804.11 Wi-Fi local network. The wireless radio 324 may also provide for connections via other wireless links or protocols, such as Bluetooth, Wi-Fi Direct, or near-field communication. The processor circuit 300 further optionally includes an illumination driver 328, which may be selectively actuated by the microprocessor 302 to supply operating current to the illuminator 110.

The processor circuit 300 further includes an audio processor 330, a microphone 332, and a speaker 334. The audio processor 330 receives and processes audio input signals from the microphone 332 and produces audio outputs at the speaker 334. The processor circuit 300 also includes a video/image processor 336 connected to the camera 108 (and the camera 108' if provided). The video/image processor 336 receives and processes image and/or video signals from the camera 108. The display 304, input device 306, memory 310, RF baseband radio 320, wireless radio 324, illumination driver 328, audio processor 330, and video/image processor 336 are all in communication with the microprocessor 302.

Figure 4:
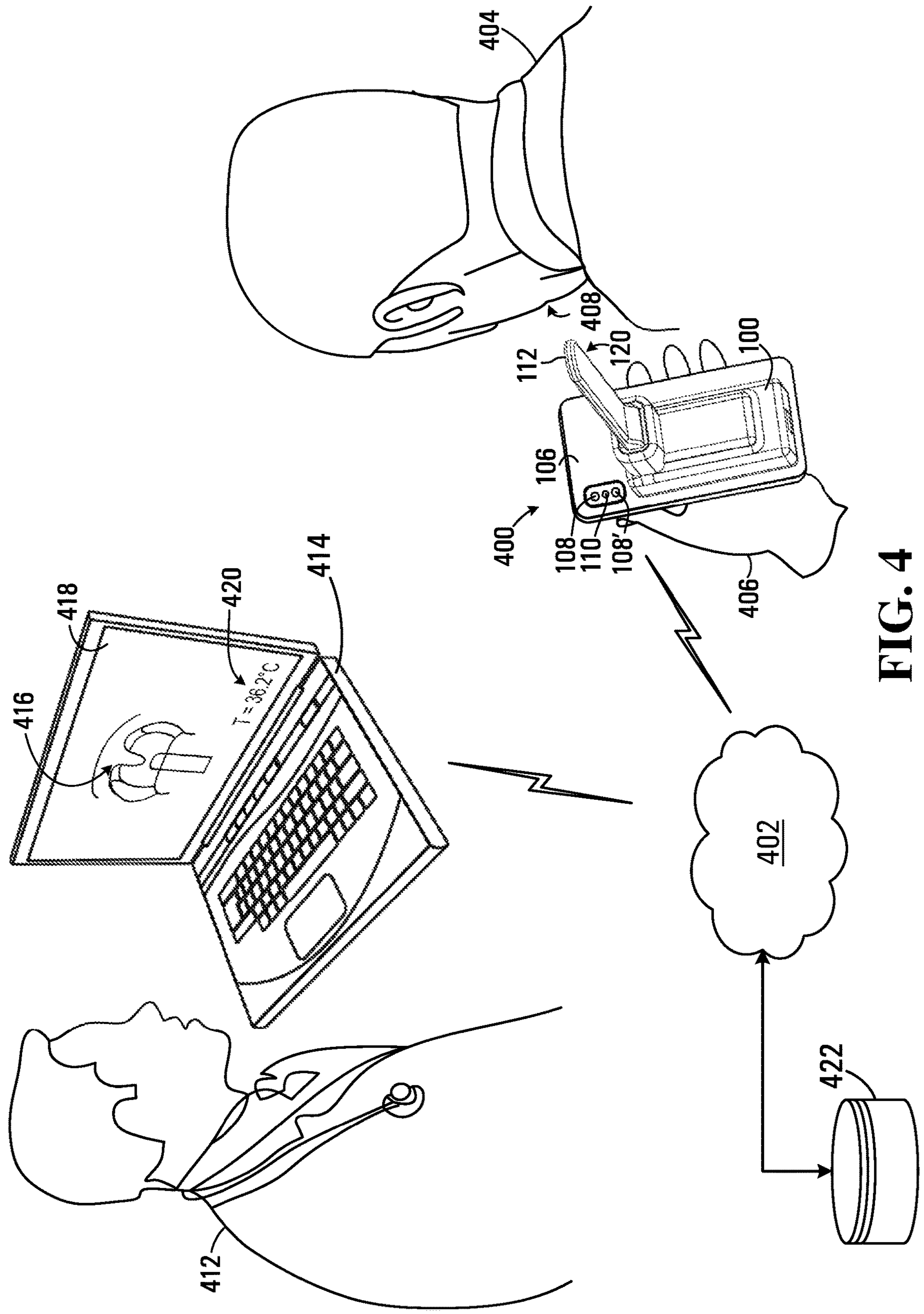
FIG. 4 is a view of the apparatus of FIG. 1A-1D in operation during a consultation session.

Operation of the apparatus 100 during a consultation session between a patient 404 and a physician 412 is described with reference to FIG. 4 and FIG. 5. Referring to FIG. 4, the patient 404 has clipped the smartphone 104 into the case 106 of the apparatus 100 generally as described above. The patient 404 has also inserted the proximal end 114 of the depressor blade 112 into the socket 116 of the mounting interface 102, such that the temperature sensor signal line conductors 134 are connected between the temperature sensor 118 and the processor board 154. The apparatus 100 and smartphone 104 together form a pharyngeal examination system 400, which is held in the patient's hand 406 with the distal end 122 of the depressor blade 112 pointed toward the patient's mouth 408.

Figure 5:
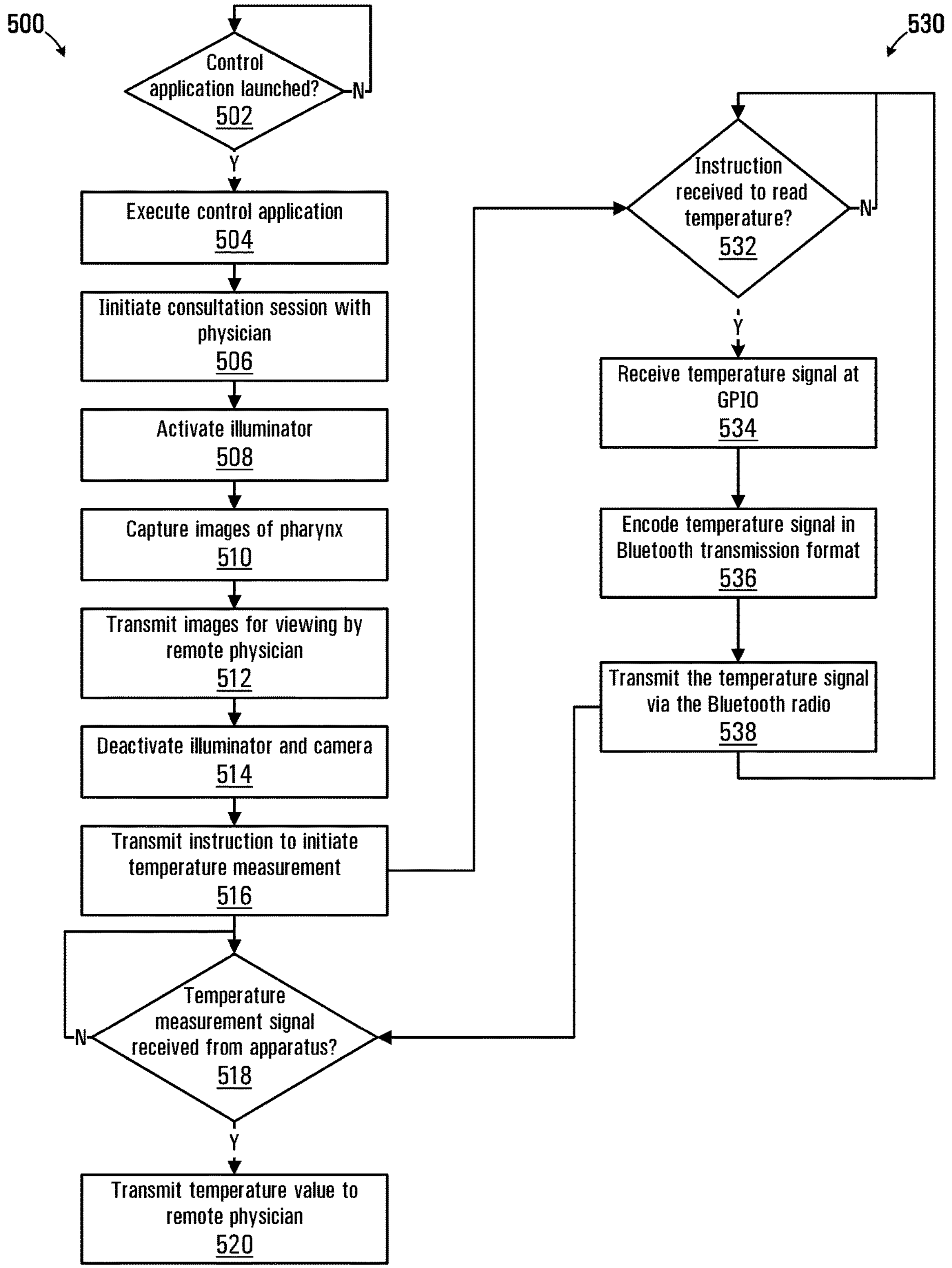
FIG. 5 is a flowchart depicting blocks of code for directing a processor circuit of the smartphone shown in FIG. 1A to perform a medical examination using the apparatus shown in FIGS. 1A-1D.

Referring to FIG. 5, a flowchart depicting blocks of code for directing the processor circuit 200 of the smartphone 104 to perform a medical examination using the apparatus 100 is shown generally at 500. The blocks generally represent codes that may be read from the storage location 314 in the memory 310 for directing the microprocessor 302 to perform various functions for completing the medical examination. The actual code to implement each block may be written in any suitable program language, such as C, C++, C #, Java, and/or assembly code, for example.

The smartphone process 500 begins at block 502 when the patient 404 launches the control application. Block 502 directs the microprocessor 302 to determine whether the patient has launched the control application, for example by determining whether an application initiation icon has been pressed on the touch screen display 304. If at block 502 the control application has not been launched, the microprocessor 302 is directed to repeat block 502. If at block 502 the control application has been launched the microprocessor 302 is directed to block 504. Block 504 directs the microprocessor 302 to execute the codes stored in the storage location 314 of the memory 310, which causes the control application to be displayed on the display 304 of the smartphone 104.

The process 500 then continues at block 506, which directs the microprocessor 302 to initiate a consultation session with a physician 412. In the embodiment shown, the physician 412 is remotely located and has access to a laptop computer 414 with a connection to a network 402 such as the internet. Block 506 directs the microprocessor 302 to use the wireless radio 324 or the RF baseband radio 320 to connect to the network 402 to establish a consultation session with the physician 412. In one embodiment the consultation session may facilitate voice and/or video communication with the physician 412 via the smartphone 104.

The patient 404 is then directed to insert the depressor blade 112 into their mouth and to cause the distal end 122 of the depressor blade to depress the tongue. The physician 412 may provide instructions via the voice and/or video link. Alternatively, the patient 404 may be prompted to insert the depressor blade 112 by the control application running on the smartphone 104. The process 500 then continues at block 508, which directs the microprocessor 302 to cause the illumination driver 328 to activate the illuminator 110. The depressor blade 112 displaces the patient's tongue downwardly thus facilitating illumination of the pharynx by the illuminator 110.

Block 510 then directs the microprocessor 302 to cause the camera 108 to capture images of the illuminated pharyngeal area, which are processed through the video/image processor 336. In one embodiment the captured images may be live streamed over the network 402 to the physician's computer 414 and displayed at 416 on a display 418 of the laptop. Block 510 may also direct the microprocessor 302 to store the images in the data storage location 316 of the memory 310. In some embodiments the images may be streamed as a series of time separated still images. In other embodiments a video stream of images may be streamed over the network 402. In this case, the physician 412 may direct the patient 404 to change the disposition and orientation of the apparatus 100 to better capture relevant areas of the patient's pharynx. The images are displayed at 416 on the display 418 of the physician's computer 414 and the physician 412 is able to view the condition of the patient's pharynx for purposes of making a diagnosis or determining the effect of pervious treatment.

At block 514, once the physician 412 has concluded the examination, the microprocessor 302 may be directed to deactivate the illuminator and camera. In one embodiment block 514 may be executed in response to user input received from the patient 404 at the input device 306.

The process 500 then continues at block 516, which directs the microprocessor 302 to transmit an instruction to the apparatus 100 to initiate a temperature measurement. Block 516 is shown as following block 514 in FIG. 5, however in some embodiments block 514 and the successive blocks 518 and 520 may be executed prior to activating the illuminator at block 508 or may be performed in parallel with any of blocks 508-512. In one embodiment, block 514 directs the microprocessor 302 to activate Bluetooth functions provided by the wireless radio 324 and to transmit an instruction to initiate a temperature measurement.

Still referring to FIG. 5, a flowchart depicting blocks of code for directing the microcontroller 158 of the apparatus 100 to perform a temperature measurement is shown generally at 530. The blocks generally represent codes that may be programmed into the microcontroller 158 for directing the microcontroller to read the temperature sensor and transmit the temperature signal. The microcontroller process 530 starts at block 532, which directs the microcontroller 158 to determine whether a Bluetooth instruction has been received at the wireless transmitter 160 to read and transmit the temperature signal. If at block 532 the instruction has not yet been received, the microcontroller 158 is directed to repeat block 532. If at block 532 the instruction has been received, the microcontroller 158 is directed to block 534. Block 534 directs the microcontroller 158 to receive the temperature signal generated by the temperature sensor 118 at the GPIO 168. The GPIO of a microcontroller such as the microcontroller 158 generally includes interface inputs that can be used to receive or generate signals. In one embodiment, the temperature sensor 118 may generate a digital temperature signal that is received at the GPIO. In other embodiments the temperature sensor 118 may generate an analog temperature signal and the analog signal is then converted into a digital representation by an analog-to-digital converter (ADC) of the GPIO 168.

Block 536 then directs the microcontroller 158 to encode the digital temperature signal into a suitable digital data format for transmission via the wireless transmitter 160. The process then continues at block 538, which directs the microcontroller 158 to transmit the digital temperature signal to the smartphone 104 for receipt by the wireless radio 324.

The process 500 implemented on the smartphone 104 then continues at block 518, which directs the microprocessor 302 of the smartphone 104 to determine whether a temperature signal has been received at the wireless radio 324. If the temperature signal has not yet been received, block 518 directs the microprocessor 302 back to repeat block 518. If at block 518, the temperature signal has been received, the microprocessor 302 is directed to block 520 which directs the microprocessor 302 to cause the RF baseband radio 320 of the wireless radio 324 to transmit the temperature represented by the temperature signal to the physician's computer 414 via the network 402.

Referring back to FIG. 4, the digital temperature signal is received at the physician's computer 414, which causes the temperature to be displayed at 420 on the display 418. The physician 412 is thus also provided with this additional information which may be of assistance in making a diagnosis or other determination about the condition of the pharynx of the patient 404.

While the processes 500 and 530 have been described with reference to a remote physician 412, in some embodiments the physician and patient 404 may be engaged in an in-person consultation. In this case, the communications between the smartphone 104 and the physician's computer 414 may be conducted via a local network rather than over the internet. Alternatively the smartphone 104 may connect to the physician's computer 414 using Bluetooth or another wireless communication medium.

In another embodiment, the examination performed by the patient 404 may be completed in advance of the consultation session with the physician 412. In this case, the images and temperature measurement data may be stored in the data storage location 316 of the memory 310 on the smartphone 104 and uploaded to the physician's computer 414 over the network 402. Alternatively, the images and temperature measurement data may be stored in a remote storage location 422 in communication with the network 402, which can be accessed by the smartphone 104 or the physician 412 via the physician's computer 414. Image and temperature readings may be stored in the cloud storage location 422 as a record that associates the temperature with image data representing a captured image of the pharynx. Additional metadata such as the date and time, a patient name or identifier, and other data may be stored as part of the record to facilitate later review by the physician 412 of patient 404. The remote storage location may be implemented using a cloud storage service.

In one embodiment the smartphone 104 and/or the physician's computer 414 may be configured by program codes to retrieve a plurality of records including image data and associated temperatures captured over a period of time from the cloud storage location 422 and to display a series of views of the pharynx over the period of time for documenting a progression of a condition associated with the patient's pharynx.

While embodiments are described herein with reference to the processor circuit architecture 200 shown in FIG. 2, the described system embodiments and/or process embodiments are also applicable to communications between other types of devices capable of connecting to the data network 108.

Figure 6A:
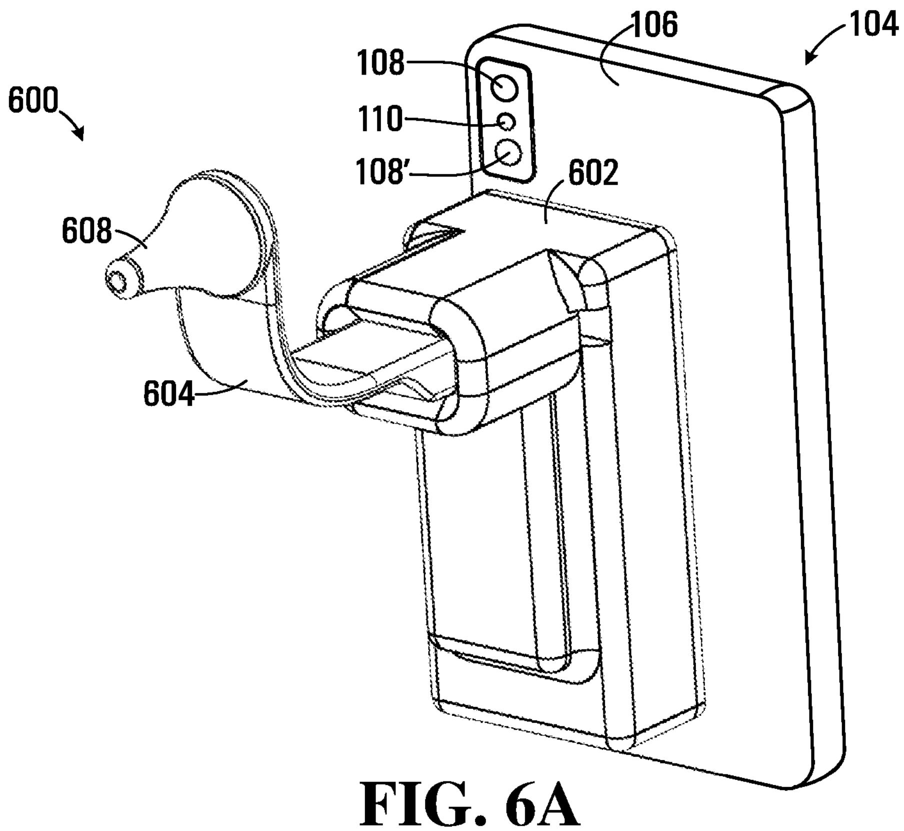
FIG. 6A is a perspective view of an apparatus for performing a medical examination of a patient's ear canal in accordance with another disclosed embodiment.

Referring to FIG. 6A, an apparatus for performing a medical examination of a patient's ear in accordance with another disclosed embodiment is shown generally at 600. The apparatus 600 is used in conjunction with the smartphone, in this embodiment the smartphone 104 in the case 106 shown in FIG. 1A. The apparatus 600 includes a mounting interface 602, which is configured to mechanically couple to the smartphone 104 as described above.

Figure 6B:
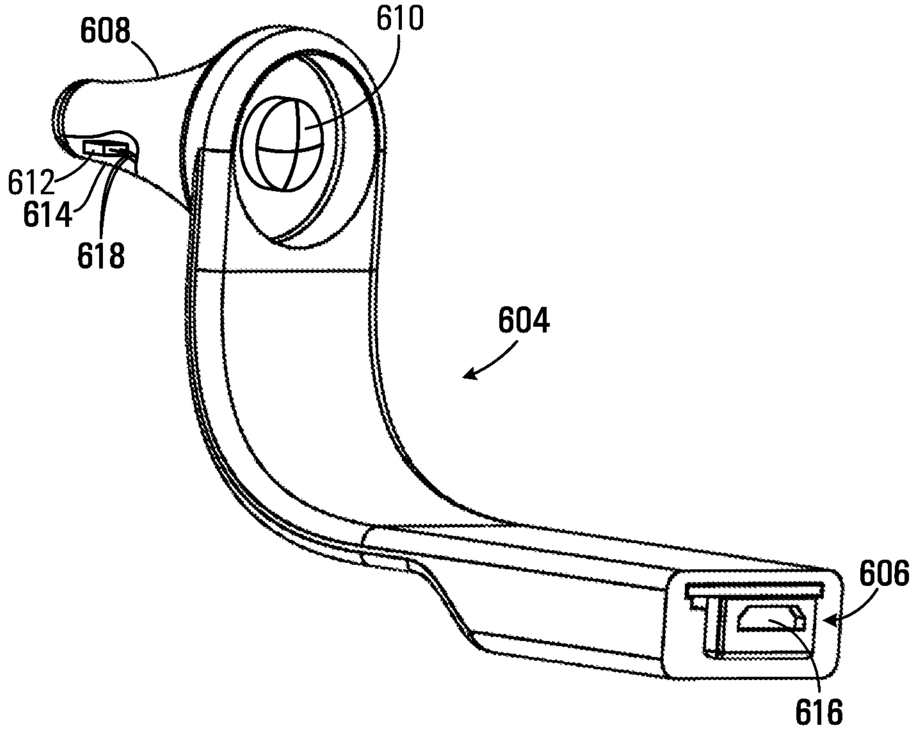
FIG. 6B is a perspective view of the apparatus of FIG. 6A showing an otoscope attachment detached from a mounting interface of the apparatus.

The apparatus 600 further includes an otoscope attachment 604, which in FIG. 6A is shown attached to the mounting interface 602. The otoscope attachment 604 is shown in isolation in FIG. 6B and includes a proximal end 606 configured to demountably attach to the mounting interface 602. In this embodiment the mounting interface 602 may be similar to the mounting interface 102 shown in FIGS. 1A, 1B and 1D. In other embodiments the mounting interface 602 may be a common mounting interface that is used to selectively receive the otoscope attachment 604 or the depressor blade 112 of FIG. 1A to 1C.

The otoscope attachment 604 terminates in a speculum 608, which is shaped for insertion into a patient's ear. The otoscope attachment 604 includes one or more optical elements 610 disposed and configured to direct illumination provided by the illuminator 110 of the smartphone 104 into the patient's ear. The one or more optical elements 610 also capture and direct light back to the cameras 108 and 108' of the smartphone 104 for generating one or more images of the ear. The speculum 608 is sized to permit sufficient insertion to permit images of the patient's ear canal and/or eardrum to be captured. The speculum 608 may be covered by a single-use speculum cover (not shown) or the entire speculum portion may be removable.

The otoscope attachment 604 further includes a temperature sensor 612 distally disposed on the speculum 608. The temperature sensor 612 is shown in partly cut-away view in FIG. 6B, and in the embodiment shown is sealingly embedded in an underside distal surface 614 of the speculum 608. The temperature sensor 612 is disposed to generate a temperature signal representing a temperature of the patient's ear when the speculum 608 is inserted for an ear examination. As disclosed above in connection with the FIG. 1A-1D embodiment, the apparatus 600 also includes a signal interface disposed within the mounting interface 602. The signal interface is configured to receive and transmit the temperature signal to the smartphone 104. The signal interface may include the processor circuit 200 described above in connection with FIG. 2.

The otoscope attachment 604 includes a signal connector 616 located at the proximal end 606. The signal connector 616 is connected via a signal line 618 to the temperature sensor 612. The signal connector 616 is configured to connect to a corresponding interface connector on the mounting interface, as described above in connection with the tongue depressor embodiment.

In operation of the apparatus 600, the smartphone process 500 may be implemented as shown in FIG. 5, except that the images captured at block 510 would be of the patient's ear rather than the pharynx. As in the case of the tongue depressor embodiment, the temperature measurement blocks 518 and 520 may be executed prior to activating the illuminator at block 508 or may be performed in parallel with any of blocks 508-512. Images of the ear captured using the apparatus 600 may also be transmitted via the network 402 to the physician 412 as shown in FIG. 4. Records may be generated associating the temperature measurement with image data representing a captured image of the ear and may be stored in a data storage location accessible by the smartphone 104 for later retrieval.

The above disclosed embodiments have the advantage of relying on the use of the smartphone 104 to provide illumination and imaging for performing the medical examination. This has the advantage of reducing the cost of the mounting interface 102 and 602. The temperature sensors 118 and 612 provide additional information on the patient's condition at the same time the examination is being performed.

While specific embodiments have been described and illustrated, such embodiments should be considered illustrative only and not as limiting the disclosed embodiments as construed in accordance with the accompanying claims.

What is claimed is:

1. An apparatus for use with a smartphone for performing a medical examination of a pharynx of a patient, the smartphone including a camera and an illuminator, the apparatus comprising:
- a mounting interface configured to mechanically couple to the smartphone;
- a depressor blade including a proximal end configured to demountably attach to the mounting interface and a signal connector located at the proximal end, the depressor blade being configured to displace a tongue of the patient to provide access for illumination of the pharynx by the illuminator, the illumination facilitating capture of an image of the pharynx by the camera, the signal connector being configured to connect to an interface connector on the mounting interface;
- a temperature sensor disposed on the depressor blade for generating a temperature signal representing a temperature in the pharynx, the temperature sensor being connected to the signal connector via a signal line; and
- a signal interface disposed within the mounting interface, the signal interface being configured to receive and transmit the temperature signal to the smartphone.

2. The apparatus of claim 1 wherein the signal connector and the interface connector comprise one of:
- corresponding Universal Serial Bus (USB) connector types; or
- a printed circuit board edge connector and corresponding socket connector.

3. The apparatus of claim 1 wherein the mounting interface comprises a socket configured to receive and guide the proximal end of the depressor blade to cause the signal connector to connect to the interface connector.

4. The apparatus of claim 1 wherein the temperature sensor is distally disposed proximate an underside of the depressor blade to facilitate thermal contact with the tongue while the depressor blade displaces the tongue.

5. The apparatus of claim 1 wherein the signal interface comprises:
- an electrical circuit for receiving the temperature signal and generating data representing the temperature signal; and
- a wireless transmitter for transmitting the data representing the temperature signal to the smartphone.

6. The apparatus of claim 5 wherein the signal interface further comprises a power source operable to supply operating current to the electrical circuit and the wireless transmitter.

7. The apparatus of claim 1 wherein the mounting interface is configured to mechanically couple to the smartphone such as to provide an unobstructed field of view for the illuminator and the camera.

8. The apparatus of claim 1 wherein the mounting interface is configured to mechanically couple to the smartphone by one of:
- magnetically coupling to the smartphone;
- one or more attachment features configured to clip the mounting interface to the smartphone; or
- an integrated smartphone case configured to receive and retain the smartphone.

9. The apparatus of claim 1 wherein the depressor blade comprises a single-use depressor blade that is discarded after use.

10. The apparatus of claim 1 wherein the temperature sensor is sealingly embedded within the depressor blade to facilitate cleaning for reuse of the depressor blade after being used to depress the tongue.

11. The apparatus of claim 1 wherein at least a portion of the depressor blade comprises one of:
- a light transmissive material for transmitting at least a portion of the illumination to the pharynx; or
- one or more optical fibers extending along the depressor blade for transmitting at least a portion of the illumination to the pharynx.

12. The apparatus of claim 1 wherein the depressor blade further comprises an attachment area configured to hold a pharyngeal swab for taking a sample from the pharynx of the patient.

13. The apparatus of claim 12 wherein the pharyngeal swab comprises one of:
- a pH test strip for sensing a pH associated with the pharynx; or
- a swab for taking a sample for sensing a pathogen within the pharynx.

14. A pharyngeal examination system comprising the apparatus of claim 1 and a smartphone apparatus, the smartphone apparatus comprising a computer readable memory for storing program codes for directing a processor of the smartphone to execute functions on the smartphone to receive and display a temperature associated with the temperature signal transmitted by the apparatus.

15. The smartphone apparatus of claim 14 wherein the program codes further direct the processor to generate a record associating the temperature with image data representing a captured image of the pharynx.

16. The smartphone apparatus of claim 15 wherein the program codes further direct the processor to store the record in a data storage location accessible by the smartphone.

17. The smartphone apparatus of claim 16 wherein the program codes further direct the processor to:
- retrieve a plurality of records including image data and associated temperatures captured over a period of time; and
- display a series of views of the pharynx over the period of time for documenting a progression of a condition associated with the pharynx.

18. The smartphone apparatus of claim 16 wherein the data storage location comprises a remote storage location accessible via a data network.

19. The smartphone apparatus of claim 14 wherein the program codes further direct the processor to stream image data over a data network for viewing by a remotely located health care worker.

20. An apparatus for use with a smartphone for performing a medical examination of a patient, the smartphone including a camera and an illuminator, the apparatus comprising:

a mounting interface configured to mechanically couple to the smartphone;

a depressor blade including a proximal end configured to demountably attach to the mounting interface and a pharynx signal connector located at the proximal end, the depressor blade being configured to displace a tongue of the patient to provide access for illumination of a pharynx of the patient by the illuminator, the illumination facilitating capture of an image of the pharynx by the camera, the pharynx signal connector being configured to connect to an interface connector on the mounting interface;

a pharynx temperature sensor disposed on the depressor blade for generating a pharynx temperature signal representing a temperature in the pharynx, the pharynx temperature sensor being connected to the pharynx signal connector via a pharynx signal line;

an otoscope attachment including a proximal end configured to demountably attach to the mounting interface, the otoscope attachment terminating in a speculum shaped for insertion into an ear of the patient and including one or more optical elements disposed and configured to direct the illumination provided by the illuminator of the smartphone into the ear and to capture and direct light back to the camera of the smartphone for producing an image of the ear;

an ear temperature sensor distally disposed on the speculum for generating an ear temperature signal representing a temperature in the ear; and a signal interface disposed within the mounting interface, the signal interface being configured to receive and transmit the pharynx temperature signal when the depressor blade is attached to the mounting interface and/or the ear temperature signal when the otoscope attachment is attached to the mounting interface to the smartphone.

21. The apparatus of claim 20 wherein:

the otoscope attachment comprises an ear signal connector located at the proximal end, the ear signal connector being connected via an ear signal line to the ear temperature sensor, the ear signal connector being configured to connect to the interface connector on the mounting interface.

22. The apparatus of claim 21 wherein the pharynx signal connector, the ear signal connector and the interface connector comprise one of:

corresponding Universal Serial Bus (USB) connector types; or a printed circuit board edge connector and corresponding socket connector.

23. The apparatus of claim 21 wherein the mounting interface comprises a socket configured to receive and guide the proximal end of the depressor blade to cause the pharynx signal connector to connect to the interface connector and/or to receive and guide the proximal end of the otoscope attachment to cause the ear signal connector to connect to the interface connector.

24. The apparatus of claim 20 wherein:

the pharynx temperature sensor is distally disposed proximate an underside of the depressor blade to facilitate thermal contact with the tongue while the depressor blade displaces the tongue; and/or the ear temperature sensor is distally disposed proximate an underside of the speculum to facilitate thermal contact with the ear.

25. The apparatus of claim 20 wherein the signal interface comprises:

an electrical circuit for receiving the pharynx temperature signal and/or the ear temperature signal and generating data representing the pharynx temperature signal and/or the ear temperature signal; and a wireless transmitter for transmitting the data representing the pharynx temperature signal and/or the ear temperature signal to the smartphone.

26. The apparatus of claim 25 wherein the signal interface further comprises a power source operable to supply operating current to the electrical circuit and the wireless transmitter.

27. The apparatus of claim 20 wherein the mounting interface is configured to mechanically couple to the smartphone such that the illumination provided by the illuminator of the smartphone is directed into the pharynx and/or the ear via the one or more optical elements and the light captured by the one or more optical elements is directed toward the camera of the smartphone.

28. The apparatus of claim 20 wherein the mounting interface is configured to mechanically couple to the smartphone by one of:

magnetically coupling to the smartphone;

one or more attachment features configured to clip the mounting interface to the smartphone; or an integrated smartphone case configured to receive and retain the smartphone.

29. The apparatus of claim 20 wherein:

the depressor blade comprises a single-use depressor blade that is discarded after use; and/or the otoscope attachment comprises a single-use speculum cover that is discarded after use.

30. The apparatus of claim 20 wherein:

the pharynx temperature sensor is sealingly embedded within the depressor blade; and/or the ear temperature sensor is sealingly embedded within a tip of the speculum.

31. An examination system comprising the apparatus of claim 20 and a smartphone apparatus, the smartphone apparatus comprising a computer readable memory for storing program codes for directing a processor of the smartphone to execute functions on the smartphone to:

receive and display a temperature associated with the pharynx temperature signal transmitted by the apparatus when the depressor blade is attached to the mounting interface; and/or receive and display a temperature associated with the ear temperature signal transmitted by the apparatus when the otoscope attachment is attached to the mounting interface.

32. The smartphone apparatus of claim 31 wherein the program codes further direct the processor to generate a record associating the temperature with image data representing a captured image of the pharynx when the temperature is associated with the pharynx temperature signal and/or a captured image of the ear when the temperature is associated with the ear temperature signal.

33. The smartphone apparatus of claim 32 wherein the program codes further direct the processor to store the record in a data storage location accessible by the smartphone.

34. The smartphone apparatus of claim 33 wherein the program codes further direct the processor to:

retrieve a plurality of records including image data and associated temperatures captured over a period of time; and display a series of views of the pharynx over the period of time for documenting a progression of a condition associated with the pharynx and/or a series of views of the ear over the period of time for documenting a progression of a condition associated with the ear.

35. The smartphone apparatus of claim 33 wherein the data storage location comprises a remote storage location accessible via a data network.

36. The smartphone apparatus of claim 31 wherein the program codes further direct the processor to stream image data over a data network for viewing by a remotely located health care worker.

* * * * *